US00PP16396P3

(12) United States Plant Patent
Gonzales et al.

(10) Patent No.: US PP16,396 P3
(45) Date of Patent: Mar. 28, 2006

(54) PINEAPPLE PLANT NAMED 'P-1972'

(50) Latin Name: *Ananas comosus*
Varietal Denomination: P-1972

(75) Inventors: Jorge Gonzales, San José (CR); Jerry Vriesenga, Wahiawa, HI (US)

(73) Assignee: Dole Food Company, Inc., Westlake Village, CA (US)

( * ) Notice: Subject to any disclaimer, the term of this patent is extended or adjusted under 35 U.S.C. 154(b) by 79 days.

(21) Appl. No.: 10/871,846

(22) Filed: Jun. 17, 2004

(65) Prior Publication Data

US 2005/0283863 P1 Dec. 22, 2005

(51) Int. Cl.
*A01H 5/00* (2006.01)

(52) U.S. Cl. ..... Plt./156
(58) Field of Classification Search ..... Plt./156
See application file for complete search history.

(56) References Cited

U.S. PATENT DOCUMENTS

PP8,863 P 8/1994 Oda ..... Plt./156

*Primary Examiner*—Anne Marie Grunberg
*Assistant Examiner*—June Hwu
(74) *Attorney, Agent, or Firm*—Morrison & Foerster LLP

(57) ABSTRACT

A new pineapple (*Ananas comosus*) variety of the Bromeliaceae family was developed from a cross between the parental lines 64-337 (C12Q2SG1P1)×59-443 (C9P3SG2R2) and has been designated 'P-1972'. This new variety differs from its progenitors in having higher carotene content, improved aroma, distinct fruit and flesh colors, and very symmetrical, oval fruit shape. It also shows low incidence of fruitlet core rot and marbling. The plant is characterized by long spineless leaves with piping, pale to grayish green in color, with veins protruding from the leaf surface. The plant has a uniform cylindrical and symmetrical fruit with a smooth and thin shell and flat fruitlets or eyes. Fruit is borne on a peduncle and the crown is long and conical with green to grayish green leaves. When unripe, fruit shell is pale green, turning to uniform yellow color when ripe. The flesh color is orange-yellow to yellow.

3 Drawing Sheets

FIELD OF THE INVENTION

Botanical/commercial classification: *Ananas comosus*/ "Gold-type" pineapple variety.

Varietal denomination: cv. P-1972.

The invention refers to a new plant variety of pineapple (*Ananas comosus*) family Bromeliaceae, subclass of Monocotyledons, and named 'P-1972'. This new variety has a distinctly oval shaped fruit, with a very thin shell, higher carotene content, which gives a darker color to the pulp. It also has higher soluble solids and acidity, and distinct flavor and aroma profiles compared to other varieties.

BACKGROUND OF THE INVENTION

In 1975, a new pineapple variety was selected as an individual plant from a segregating population produced from seed from a cross made in Hawaii in 1972. The new variety was known as '75-80.' '75-80' contains at least 50% genetic base from Cayenne pineapple. The parental lines included two clones previously developed by the Pineapple Research Institute (PRI), namely '64-337' (C12Q2SG1P1)× '59-443' (C9P3SG2R2). Testing and selection of individual plants took place in Honduras, Central America.

Parental Description: Seed parent hybrid '64-337' was originally developed in the Pineapple Research Institute in Hawaii, from where it was introduced into Honduras for field evaluation. Genetically '64-337' is composed of ¾ Cayenne, ⅛ Queen, 1/16 Smooth Guatemala, and 1/16 Pernambuco. '64-337' is not patented. This hybrid clone is less susceptible to premature flowering (NDF) as compared to Cayenne variety. It has also shown greater tolerance to the internal brown spot disorder (IBS). IBS is internal brown spotting of the pulp. The plant has spineless leaves of a light green color. Fruit pulp shows yellow color with high carotene content.

Pollen parent 59-443 is a hybrid clone developed at the Pineapple Research Institute in Hawaii, and it was introduced to Honduras during the early 1970's. '59-443' is not patented. Under Montecristo conditions, (Montecristo Farm, property of Standard Fruit de Honduras, located in the North coast of Honduras) '59-443' is resistant to natural differentiation of flowers (NDF), it develops a semi-erect plant habit, produces one to two slips per plant and is susceptible to lodging. Compared with Smooth Cayenne, leaves are narrower, longer in shape and spineless. Leaf color is dark green with reddish along the margins. Petal color is purple in the tip and whitish at the base. Fruit peduncle is medium, shape is long conical to cylindrical with broad fruitlets and fruit size is smaller than Cayenne. Flesh color is golden yellow. '59-443' Hybrid clone is susceptible to *Phytophthora parasitica*, but has shown tolerance to IBS disorder.

This breeding effort aimed to produce a fresh fruit variety with good fruit size and shape as well as high canning potential. Year round production, a reduced propensity to premature flowering (NDF resistance), lower incidence of internal brown spot disorder (IBS), high carotene, higher Vitamin C, stable crown type and good flavor relative to the commonly grown 'Smooth Cayenne' variety, were a few of the key selection parameters.

The development of the new variety started in Wahiawa, Hi. Flowers of clone '64-337' were cross-pollinated with pollen taken from plants of clone '59-443' in 1972. Seeds from this cross were taken to Honduras in 1974 for germination and subsequent selection of promising individuals. Since then, the variety has been under cultivation at the Montecristo Farm, property of Standard Fruit de Honduras, located in the North coast of Honduras. Different methods of asexual propagation were used for variety multiplication, i.e. stem cuttings, slips, suckers, propagules, fruit crown and tissue culture derived plants.

The selected hybrid showed unique characteristics such as distinctive fruit aroma and deep yellow color in both shell and flesh, as well as a very symmetrical, oval fruit shape. The plants were further propagated using slips, hapas, crowns, and stem cuttings and augmented over the years in number. The new hybrid was designated '75-80'. Elite individuals showing shorter peduncles and larger fruit were selected in 2001 from the original population of '75-80' and designated 'P-1972'. The present description covers the new population of elite plants with improved characteristics designated as 'P-1972'. The new cultivar is stable and has reproduced true to type in three successive generations of asexual reproduction.

SUMMARY OF THE INVENTION

The new pineapple (*Ananas comosus*) variety, 'P-1972', differs from its parents in having higher carotene content, improved aroma, distinct fruit and flesh colors, and very symmetrical, oval fruit shape. It also shows low incidence of fruitlet core rots, and marbling. The plant is characterized by long, spineless leaves with piping, pale to grayish green in color, with veins protruding from the leaf surface. Fruit has a smooth and thin shell and flat fruitlets or eyes.

'P-1972' has shorter peduncles and larger fruit than '75-80' and it is less prone to shell cracking. 'P-1972' has much higher levels of carotene than 'Mayan Gold 1' and 'Mayan Gold 3.' 'Mayan Gold 1' is an unpatented hybrid resulting from crosses between Pineapple Research Varieties '57-293' and '59-443.' 'Mayan Gold 3' is an unpatented Pineapple Research Institute hybrid designated '73-114' resulting from a cross between PRI '58-1184' and PRI '59-443'. The 'P-1972' fruit shape is egg (oval) shaped as compared to square shouldered or cylindrical shape of 'Mayan Gold 3.' 'Mayan Gold 1' has red pigmentation on the leaves, whereas Mayan Gold 3 and 'P-1972' do not. 'P-1972' is lighter green than 'Mayan Gold 3' under a variety of growing conditions. In addition, 'P-1972' has higher carotene, Brix and acid than 'Mayan Gold 3,' under a variety of growing conditions.

BRIEF DESCRIPTION OF THE DRAWINGS

The accompanying photographs depict some of the differences between 'P-1972' and '75-80'.

BOTANICAL DESCRIPTION OF THE PLANT

Figure 1:
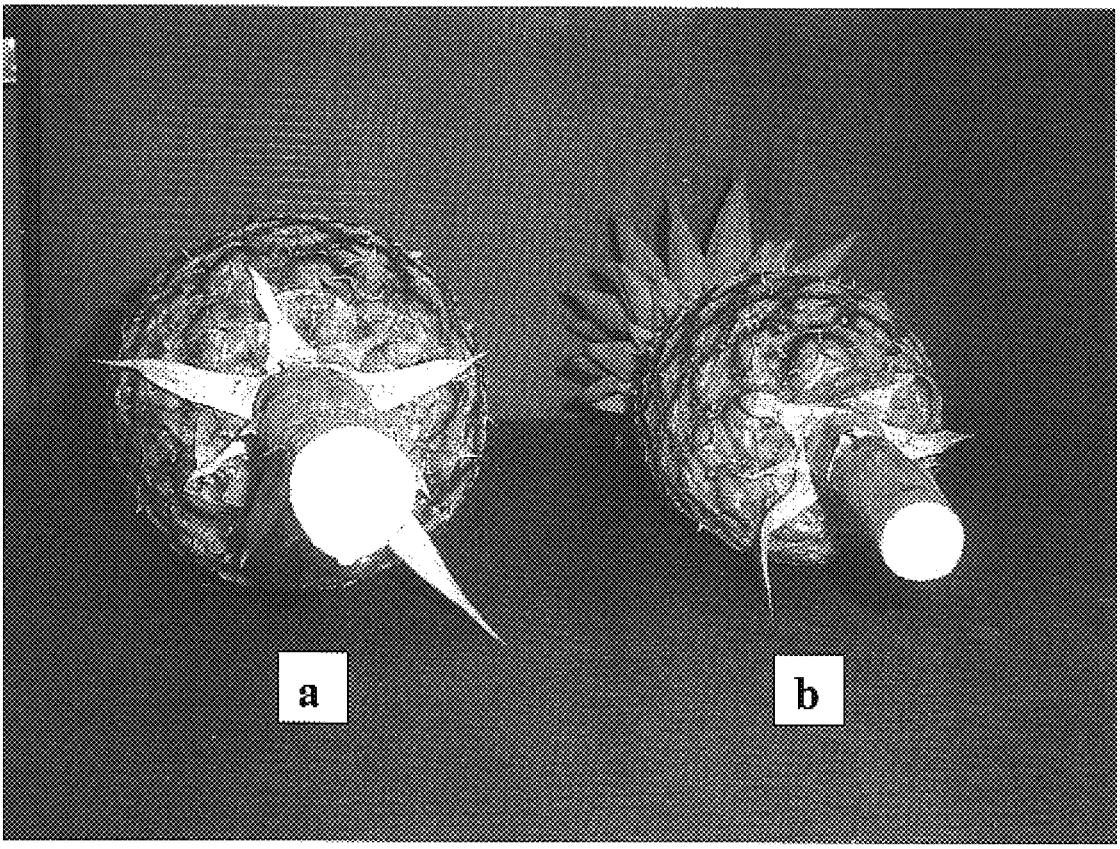
FIG. 1 shows 'P-1972' (a) compared to '75-80' (b).
Figure 2:
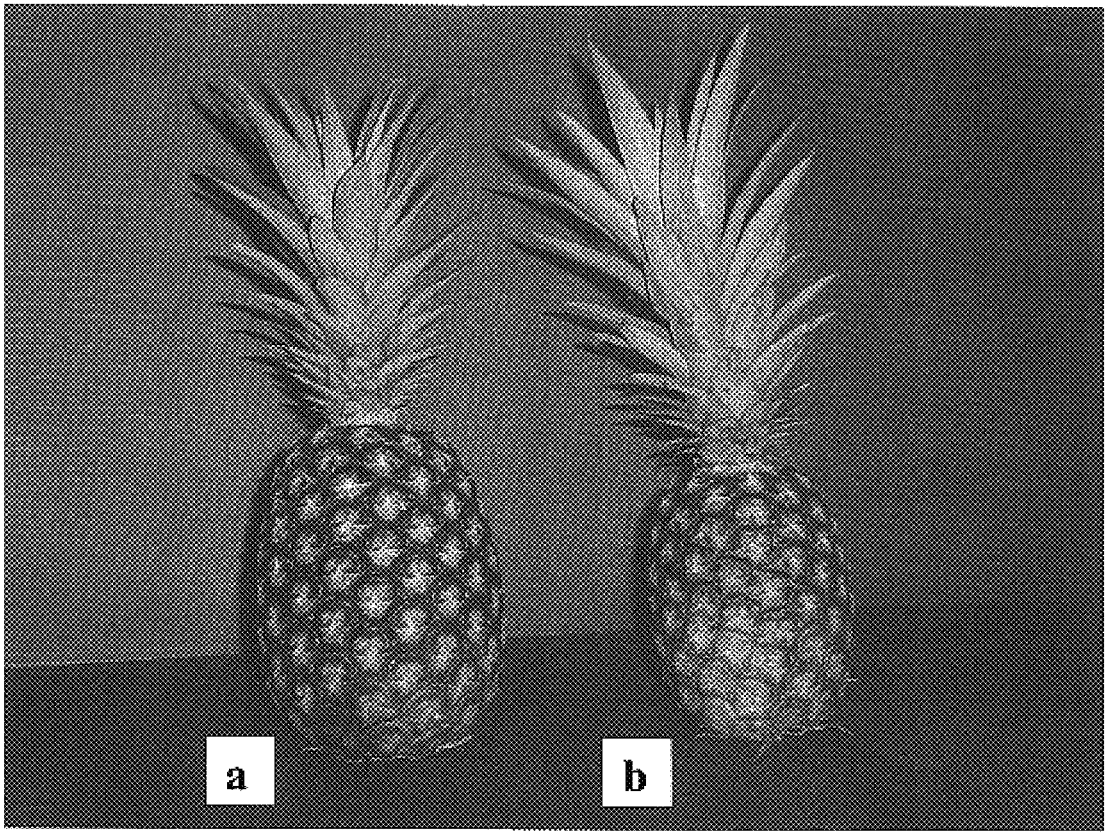
FIG. 2 shows 'P-1972' (a) compared to '75-80' (b).
Figure 3:
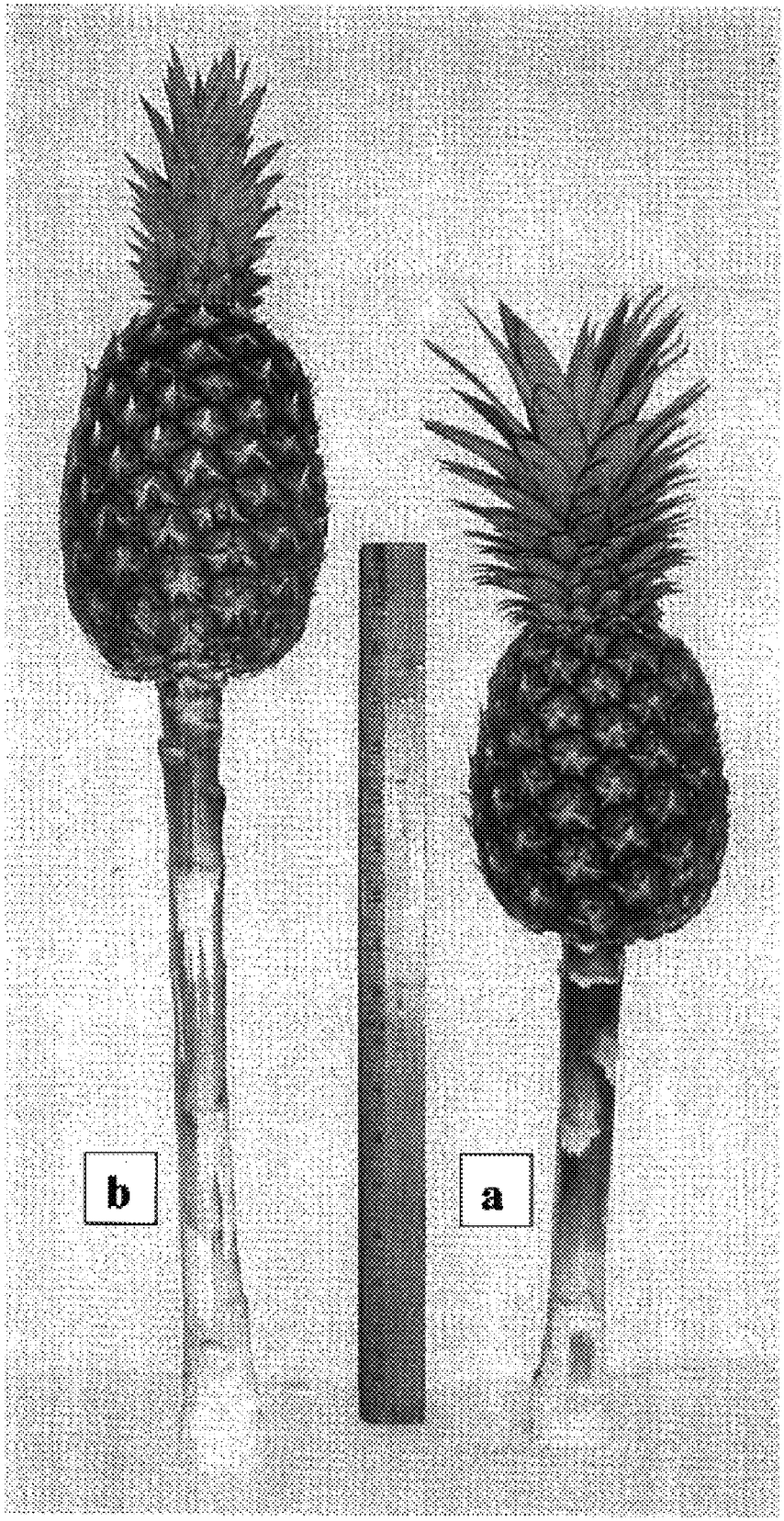
FIG. 3 shows 'P-1972' (a) compared to '75-80' (b).

The following detailed description of the new plant variety is based on observations of well-fertilized specimens at the vegetative stage (314 days after planting) and inflorescence development (384 days after planting) and fruit harvesting (468 days after planting) in the months of October to December, 2003, grown in two different locations. First at Montecristo farms, in the Northern coast of Honduras (15 degrees 44 minutes latitude north, and 86 degrees 53 minutes longitude west). Also included are observations from plants grown in the Atlantic slope in Costa Rica (El Bosque farm, 10 degrees 52 minutes, latitude north; and 84 degrees 73 minutes, longitude west). Average temperature in Montecristo is 26° C., and 3542-mm average annual precipitation, whereas temperature in El Bosque averages 25° C., with annual rainfall of 3217-mm.

The color of plant specimens and tissues are referred to the terminology and designations reported in the Munsell Color Charts for plant tissues, published by Gretag Macbeth LLC, New Windsor, N.Y. Color chart and colors were reported in terms of hue value and chroma notation.

The following is a description of a population of plants of the new variety grown at Montecristo, and El Bosque Farms, in Honduras and Costa Rica respectively (numbers in parenthesis are for plants grown in Costa Rica).

Name: *Ananas comosus* (L.) Merr. Var. P-1972, family Bromeliaceae, subclass Monocotyledons.

Parentage:

*I. Seed parent.*—Clone '64-337'.

*II. Pollen parent.*—Clone '59-443'. Origin: a PRI cross between clones '64-337' and '59-443'.

Classification:

*Botanic.*—Family: Bromeliaceae family. Subfamily: Bromeliacidae. Genus: *Ananas*. Species: *comosus*. Cultivars: '64-337'×'59-443' (var. P-1972).

Commercial: Bromeliad fruit plant.

*General form.*—The aerial part of the 'P-1972' plant has an open foliage and consists of a compact rosette of overlapping sessile leaves arising from a central stem and surrounding a composite inflorescence during anthesis. On average the number of offshoots of different kind (hapas, suckers and slips), initiated during or after anthesis are 1.1, 0.1 and 0.1–5.3 respectively. Dominant offshoots produce subsequent crops after initial fruit harvest. Plant height is considered normal, measuring on average 86.4±14.0 cm, including the fruit (Costa Rica — 93.9±3.1). Mean stem diameter is 5.6±1.1 cm, measured at the base and at harvest time.

*Stems.*—Stems peduncle are upright and short, usually 20.6±3.9 cm in height, and 7.5±1.4 cm in diameter at flowering. Stems are sheathed by overlapping leaves arranged in acropetal fashion, forming a heart shape stem. The stem color is pale green (5 GY 7/8 to 7/10).

Leaves:

*General.*—Leaves are sessile, lanceolated in form, very elongated and succulent, with acuminate apex shape, and, forming a rosette with a 5/13 phyllotaxy. Foliage attitude is rather open, with leaf breakage of medium resistance. The surface texture of the leaves is smooth despite the presence of trichomes on both epidermises. The number of leaves per plant ranges between 44.2±5.6 to 54.7±4.2, (Costa Rica — 56±5) with dormant axillary buds at the base of each leaf.

*Color.*—The color of the upper surface of the 15th leaf from the top, determined by Munsell chart for plant tissue, ranges from pale green (varying from 5 GY 6/6, 6/8, 7/6, 7/8, 5/10) to dark green (5 GY 4/4, 4/6, 4/8, 5/6, 5/8).

*Margins.*—The leaves are completely spineless showing the presence of piping, which is due to a portion of the lower epidermis being folded over the upper leaf surface. The piping seem from the upper side presents a olive-green color (5 GY 6/6 to 6/8) and on the underside a grayish-olive color is observed (5 GY 5/4 to 5/6). Thickness in the longest lead is 1.5±0.4 mm on average.

*Insertion angle.*—58.9±4° for the 14th leaf from the youngest one, in 2.3 kg plants grown at a planting distance of 16 inches between rows and 10 inches between plants.

*Leaf size.*—Fully developed leaves range from 106.6±6.7 cm to 130.1±4 cm in length and 6.3±0.4 to 7.6±0.9 cm in width.

*Leaf venation.*—Parallel with an especial band that stick out in both leaves surfaces.

Inflorescence:

*General.*—Pineapple inflorescence of composite flower, with self-incompatible individual bi-sexual flowers containing three sepals (9.1±1.1 mm in length), six stamens (14.6±0.9 mm in length), three stigmas (1.5±0.4 mm wide), and three carpels (5.3±0.8mm wide). The inflorescence is borne in a long peduncle, 20.6±3.9 cm in length, and with light-green to green coloration (7.5 GY 7/8 to 7/10, 5/6 to 5/8). Each inflorescence is composed of 84 to 138 fruitlets. Average size of the inflorescence at mid flower stage is 6.0±0.5 cm in diameter, and 10.5±0.5 cm in height.

Floral bracts are lanceolated with smooth edge aspect, covering one third of the fruitlet (18±1.6 mm in length, and 15.8±1.9 mm at the base). Bract's apex is aristate with a truncate base. In unripe fruit the bracts color is a pale green (5 GY 6/8) in the outside, whereas bract tip color in ripe fruit is deep pink (5 R 6/10, 6/8) in the inside.

Sepals are of orbicular shape and with olive-green color in the adaxial side of base (5 GY 6/8 to 6/10).

Petals are oblong is shape with color varying from purple (5 RP 4/4) on the tip, white purple (5 RP 4/10, 4/12) in the center, and whitish on the bottom. The color of pollen is yellow (5Y 8/8 to 8/10).

Fruit:

*Fruit shape.*—The fruit is uniform cylindrical and symmetrical, slight taper with a diameter of 12.1±0.7 cm (Costa Rica — 10.9±2.0 cm). The shell is smooth and thin, with flat fruitlet eyes. Fruitlets per fruit varies depending on fruit size, ranging from 113 to 146, whereas the fruitlet average number in the longest spiral is 13.1±2.3 (Costa Rica — 10 to 19).

Fruit and crown average heights are 15.4±3.2 and 17.2±4.1 cm (Costa Rica — 11.7±2.7 and 11.8±0.6 cm) respectively for a fruit/crown ratio of 0.9. Mean fruit weight ranges from 1.9–2.4 Kg (Costa Rica — 1.57±0.43 Kg), whereas crown weight varies from 0.18±0.02 to 0.26±0.05 Kg.

Color: Unripe fruitlet color is green (7.5 GY 4/2, 3/2). When the fruitlet is ripe (grade 5) the color is golden yellow (2.5 Y 8/10, 8/8 7/8, 7/10). Fruit core diameter is 2.7±0.7 cm.

Crown characteristics: The crown is long conical in shape. Leaf color is green (5GY 5/6, 5/8, 4/8). Leaves are spineless and smooth, with piping in leaf margins.

Flesh and juice characteristics (grade 5): The flesh is compact, dense, smooth texture with small amount of fibers and distinct mango-like aroma. Occasionally few seed (1–5) are found. Flesh color is orange-yellow to golden yellow (2.5 Y 8/8, 8/10) and with acceptable translucency appearance. Core diameter is 2.7±0.7 cm on average, and has an orange yellow color (2.5 Y 8/6 to 8/8). Juice pH is 3.7 on average, with a Brix value of 15.3±1.3 degrees and acid value of 0.53±0.1. Ascorbic acid (mg AA/100 ml juice by indophenol method) is in the range of 22.8 to 27.5, citric acid content varies from 0.58 to 0.62.

Peduncle: Fruit develops from the apical meristem of the plant on a peduncle, usually 20.6±3.9 cm in length and 3.3±0.7 cm in diameter. Peduncle bract number is 8.1±1.4 cm, and the length of the longest bract is 20±4.6 cm.

TABLE 1

Comparison of fruit quality characteristics at maturity grade 3 between 'P-1972' and other known varieties under Montecristo farm conditions.

| Pineapple Variety | Brix | Acid (%) | Brix/Acid Ratio | Carotenoids (ppm) | Ascobic Acid (mg/100 ml) |
|---|---|---|---|---|---|
| P-1972 | 15.3 | 0.53 | 29 | 11.8 | 25 |
| Tropical Gold | 13.8 | 0.66 | 21 | 6.18 | 55 |
| Mayan Gold 01 | 13.4 | 0.63 | 21 | 2.39 | 19 |
| Champaka | 14.0 | 0.76 | 19 | 2.39 | 19 |
| Manzana | 11.5 | 0.79 | 15 | 2 | 47 |
| Castilla | 18.9 | 1.23 | 15 | 2.36 | 42 |
| Santa Marta | 13.8 | 0.74 | 19 | 4.1 | 59 |
| Red Spanishg | 14.9 | 0.97 | 15 | 2.26 | 7 |
| McGregor | 16.6 | 0.55 | 30 | 6.32 | 27 |
| Monte Lirio | 13.1 | 0.49 | 27 | 10.5 | 23 |
| Snack Pine | 20.9 | 0.33 | 64 | 7.06 | 15 |

TABLE 2

Tolerance of 'P-1972' and other pineapple varieties to certain pests and diseases and to natural flowering under Montecristo farm conditions.

| Condition | 'P-1972' | Tropical Gold | Mayan Gold 01 | Champaka |
|---|---|---|---|---|
| *Phytopthora* | moderate | low | high | high |
| *Erwinia* | moderate | low | high | high |
| Army worm | low | none | low | low |
| Mealybug (*Pseudococcus brevipes*) | low | none | low | low |
| Natural Flowering | high | low | moderate | moderate |

What we claim is:

1. The new and distinct variety of pineapple plant designated 'P-1972' substantially as shown and described herein.

* * * * *